United States Patent
Dubois

(10) Patent No.: US 10,654,798 B2
(45) Date of Patent: May 19, 2020

(54) PROCESS FOR CONTINUOUS INDUSTRIAL SYNTHESIS OF ALKANE-SUPHONICACID

(71) Applicant: Arkema France, Colombes (FR)

(72) Inventor: Jean-Luc Dubois, Colombes (FR)

(73) Assignee: ARKEMA FRANCE, Colombes (FR)

( * ) Notice: Subject to any disclaimer, the term of this patent is extended or adjusted under 35 U.S.C. 154(b) by 27 days.

(21) Appl. No.: 16/288,870

(22) Filed: Feb. 28, 2019

(65) Prior Publication Data

US 2019/0276394 A1 Sep. 12, 2019

(30) Foreign Application Priority Data

Feb. 14, 2018 (FR) ...................... 18 51230

(51) Int. Cl.
*C07C 303/06* (2006.01)
*C07C 303/04* (2006.01)
*C07C 309/04* (2006.01)

(52) U.S. Cl.
CPC .......... *C07C 303/06* (2013.01); *C07C 309/04* (2013.01)

(58) Field of Classification Search
CPC ........................... C07C 303/06; C07C 309/04
See application file for complete search history.

(56) References Cited

U.S. PATENT DOCUMENTS 7,282,603 B2 * 10/2007 Richards .................. C01B 3/34
2016/0289176 A1 * 10/2016 Ott ........................ C07C 303/06

* cited by examiner

*Primary Examiner* — Paul A Zucker
(74) *Attorney, Agent, or Firm* — Buchanan Ingersoll & Rooney P.C.

(57) ABSTRACT

A process for the continuous industrial preparation of an alkane-sulphonic acid, from the corresponding alkane and sulphur trioxide, said process being carried out in a solvent which is the alkane-sulphonic acid. The process includes e1) addition of sulphur trioxide in order to maintain an initial molar ratio (alkanesulphonic acid)/(sulphur trioxide), addition of alkane in order to maintain a molar ratio (alkane)/(sulphur trioxide) comprised between 4/1 and 2/1, and continuous withdrawal of the alkanesulphonic acid.

9 Claims, No Drawings

PROCESS FOR CONTINUOUS INDUSTRIAL SYNTHESIS OF ALKANE-SUPHONICACID

The present invention relates to the field of thiochemistry, more specifically to the industrial synthesis of sulphur derivatives, in particular of sulphonic acids, and especially of alkanesulphonic acids. More specifically, the present invention relates to a process for the industrial preparation of alkanesulphonic acid from alkanes.

The industrial synthesis processes of chemicals are constantly improved, in order to reduce risks to the environment, energy consumption, by-products, and waste products, and also to increase yields, the degrees of product purity obtained, and others.

Industrial processes for the preparation of sulphur products are not exempt from this rule. Sulphur chemistry, also called thiochemistry, is particularly targeted, due to the often toxic and odorous nature of synthetic products, intermediates, and possibly by-products formed.

The ever-increasing consumption of chemicals in the world also imposes increasingly important production capacities. In order to increase production capacity, "physical increase" (construction of new production units or expansion of existing production units) and/or a "chemical increase", can be considered, meaning a substantial modification of existing and currently used processes, in order to improve production yields, selectivity, etc., as mentioned above.

The modification or replacement of existing and currently used industrial processes does not, however, happen without posing many problems, and manufacturers require extensive testing in the laboratory and then at pilot manufacturing scale to ensure the viability of the new process on an industrial scale.

Alkanesulphonic acids, and in particular methanesulphonic acid of formula $CH_3$—$SO_3H$, are now industrially prepared according to well-known processes and for the most part, decades old, with yields that could be improved, as well as unwanted by-products that must be treated or valorised, with associated costs that are not compatible with current economic conditions.

Despite all the efforts made in recent decades, industrial processes allowing access to alkanesulphonic acids and methanesulphonic acid in particular, are affected by many disadvantages, and/or yields that could be further improved.

There remains, therefore, a need for a simple, efficient, economical and industrially cost-effective industrial process for the preparation of alkanesulphonic acid and methanesulphonic acid in particular.

Patent applications US2006100458 and US2005070614 describe the preparation of methanesulphonic acid ($CH_3SO_3H$) from methane ($CH_4$) and sulphur trioxide ($SO_3$). The reactions described in these two documents, however, are all performed in batch mode in autoclaves, often small sizes, in an inert atmosphere, for example under nitrogen. The autoclaves are heated, for example up to about 80° C., with methane pressures ranging from 2 MPa (300 psi) to almost 10 MPa (1400 psi). It is obvious that such reaction conditions, in the presence of such synthetic reagents, render said process for the preparation of methanesulphonic acid from methane and sulphur trioxide, not feasible industrially.

However, it could be very interesting to convert methane, a natural gas, into methanesulphonic acid (AMS) in the presence of sulphur trioxide ($SO_3$).

It has now been found that it is possible to convert an alkane to the corresponding alkanesulphonic acid, for example methane to methanesulphonic acid, in the presence of sulphur trioxide, in a continuous process, in a simple, effective way with good yields. Furthermore, the process of the invention can very easily be operated on an industrial scale. The process of the invention also facilitates alkanesulphonic acid purity levels greater than 95%, or even greater than 98%.

Other advantages of the present invention will be highlighted in the following description.

Thus, according to a first aspect, the present invention relates to a process for the continuous industrial preparation of an alkane-sulphonic acid, from the corresponding alkane and of sulphur trioxide, said process being carried out in a solvent which is the said alkanesulphonic acid.

"Corresponding alkane" refers to the alkane comprising the same number of carbon atoms as the alkanesulphonic acid which is to be continuously manufactured industrially. As non-exhaustive list of examples, methane ($CH_4$) is used to prepare methanesulphonic acid ($CH_3SO_3H$), ethane ($C_2H_6$) is used to prepare ethanesulphonic acid ($C_2H_5SO_3H$), propane ($C_3H_8$) is used to prepare propanesulphonic acid ($C_3H_7SO_3H$), butane ($C_4H_{10}$) is used to prepare butanesulphonic acid ($C_3H_7SO_3H$), etc., and more generally the alkane from formula $C_nH_{2n+2}$ is used to prepare the alkanesulphonic acid of formula ($C_nH_{2n+1}SO_3H$).

The present invention thus relates to a process for the continuous industrial preparation of an alkanesulphonic acid of formula ($C_nH_{2n+1}SO_3H$), wherein "n" represents an integer comprised between 1 and 20 inclusive, preferably between 1 and 12 inclusive, more preferably between 1 and 6 inclusive, and for example, equal to 1, 2, or 3.

The process according to the present invention is particularly suitable for the continuous industrial synthesis of methanesulphonic acid from methane and sulphur trioxide.

The process according to the present invention is characterized in that it is carried out in an alkane-sulphonic acid medium, desirable for continuous preparation.

More specifically, the present invention relates to the process for the continuous industrial preparation of alkanesulphonic acid of formula $C_nH_{2n+1}SO_3H$, from the alkane of formula $C_nH_{2n+2}$ wherein n is as defined above, said process comprising at least the following steps:

a) loading of alkanesulphonic acid $C_nH_{2n+1}SO_3H$, wherein n is as defined above, in a reactor, b) heating said alkanesulphonic acid at a temperature comprised between 25° C. and 120° C., preferably comprised between 25° C. and 100° C., more preferably comprised between 25° C. and 70° C., c) introducing a quantity of sulphur trioxide so that the molar ratio (alkanesulphonic acid)/(sulphur trioxide) is comprised between 70/30 and 95/5, d) introducing the alkane under a pressure comprised between 4 MPa and 15 MPa, preferably between 5 MPa and 12 MPa, d) introducing a radical initiator, e) conducting the reaction continuously, operating simultaneously, sequentially or alternatively the following three sub-steps e1), e2) and e3):

e1) addition of sulphur trioxide in order to maintain the initial molar ratio (alkanesulphonic acid)/(sulphur trioxide) defined in step c), e2) adding alkane in order to maintain a molar ratio (alkane)/(sulphur trioxide) comprised between 4/1 and 2/1, preferably between 3.5/1 and 2.5/1, typically in order to maintain a molar ratio (alkane)/(sulphur trioxide) equal to about 3, and e3) continuous withdrawal of the alkanesulphonic acid of formula $C_nH_{2n+1}SO_3H$, and f) recovering the alkanesulphonic acid of formula $C_nH_{2n+1}SO_3H$ after optional separation of unreacted reagents, and optionally any undesired by-products.

The reaction temperature is generally comprised between 25° C. and 120° C., preferably between 25° C. and 100° C., more preferably comprised between 25° C. and 70° C., typically between 30° C. and 60° C., for example, about 50° C. The reaction temperature can of course be easily adapted by those skilled in the art depending on the type of alkane used and/or the nature of the alkanesulphonic acid to be prepared, but also the type of reactor used as well as the reaction pressure.

The reaction pressure is generally comprised between 4 MPa and 15 MPa, preferably between 5 MPa and 12 MPa, and can easily be adapted by those skilled in the art depending on the type of alkane used and/or the nature of the alkanesulphonic acid to be prepared, but also the type of reactor used as well as the reaction temperature. It is preferable to operate with an alkane pressure in order to promote the solubilisation of said alkane in the alkanesulphonic acid used as a solvent. The operation is carried out for example with a pressure close to 10 MPa when the alkane is methane and the reaction solvent is methanesulphonic acid.

The continuous industrial process of the present invention can be carried out in any type of reactor well known to those skilled in the art and adapted for this type of reaction, the starting reagents and the obtained product. Among the reactor models that are entirely appropriate and suitable for the process of the present invention, included but are not limited to, reactors equipped with a recirculation loop, often referred to as a "circular" ("loop reactors" in English), self-suction turbine reactors, reactors equipped with a venturi system, ("Spinning bed reactors" in English), tubular reactors, and other may be cited.

It is possible to use reactors having one or more of the systems indicated above. Reactors equipped with a recirculation loop are particularly well suited for the continuous industrial process according to the invention, and in particular those marketed by the Buss company, as indicated for example on the website of the said Buss company: http://www.buss-ct.com/buss_loop_reactor.html).

The radical initiator used in the process of the present invention may also be of any type known to those skilled in the art and for example selected from, but not limited to, azo-bis-iso-butyronitrile, mineral or organic peroxides such as hydrogen peroxide ($H_2O_2$), mercury sulphate ($HgSO_4$), palladium sulphate ($PdSO_4$), caesium sulphate ($Ce(SO_4)_2$), $K_2P_2O_8$, $CaO_2$, halogens such as $Br_2$, $Cl_2$, and $I_2$, in the presence of metal chlorides such as calcium chloride, iron chloride, and especially rhodium trichloride ($RhCl_3$), as well as those described in applications EP1558353, WO2015071351, WO2015071365, WO2015071371, and WO2015071455, and most particularly bis-(alkanesulfonyl) peroxides of formula $C_nH_{2n+1}$—$SO_2$—O—O—$SO_2O$—$C_nH_{2n+1}$ (where n is as defined above), the initiators of formula $C_nH_{2n+1}$—$SO_2$—O—O—$SO_2OX$ (where n is as previously defined and X represents hydrogen, an alkali or alkaline earth metal, zinc or aluminium), Caro acid (HO—$SO_3$—OH) and its salts with one or more alkali or alkaline earth metals, and Marshall acid (HO—$SO_3$—$SO_3$—OH) and its salts with one or more alkali or alkaline earth metals, for example its potassium di-salt $K^+,^-O$—O—$SO_3$—$SO_3$—$O^-,K^+$.

Some initiators, such as Marshall acid, can be generated in situ. In the case of Marshall acid, it can be generated in situ by reaction between sulphur trioxide and hydrogen peroxide.

It is particularly preferred to use the initiators of formula $C_nH_{2n+1}$—$SO_2$—O—O—$SO_2O$—$C_nH_{2n+1}$ (where n is as defined above), the initiators of formula $C_nH_{2n+1}$—$SO_2$—O—O—$SO_2OX$ (where n is as defined above and X is hydrogen, an alkali or alkaline earth metal, zinc or aluminium), Caro acid (HO—$SO_3$—OH) and its salts with one or more alkali or alkaline earth metals, and Marshall acid (HO—$SO_3$—$SO_3$—OH) and its salts with one or more alkali or alkaline earth metals, for example its potassium di-salt $K^+,^-O$—$SO_3$—$SO_3$—$O^-,K^+$.

It may be advantageous to dissolve the initiators which are in solid form, before introducing them into the reaction medium. The dissolution can be carried out in any solvent compatible with said reaction medium, for example in a protic solvent, which can be the solvent of the reaction itself or water.

The alkane of formula $C_nH_{2n+2}$, where n is as defined above, is then added in order for the reaction with the sulphur trioxide in the alkane-sulphonic acid solvent to begin. It should be understood that the initiator can be added before and/or after and/or during the initial introduction of the alkane.

Alkane can be introduced in liquid or gaseous form. For example, when the alkane is methane, it can be introduced by bubbling in the solution of sulphur trioxide in methanesulphonic acid.

The reactor useful for the process of the present invention may be equipped with any stirring system well known to those skilled in the art, and for example, and included but are not limited to, one or more systems selected from propeller stirrers, circulation pumps, and in the case of tubular reactors, baffles, oscillatory systems, and others.

It should also be understood that the amount of alkanesulphonic acid formed depends on the amount of alkane introduced, while maintaining the molar ratio (alkane of formula $C_nH_{2n+2}$)/(sulphur trioxide) comprised between 4/1 and 2/1, preferably between 3.5/1 and 2.5/1, typically about 3, and maintain the molar ratio (alkanesulphonic acid)/(sulphur trioxide) between 70/30 and 95/5.

The process according to the invention in a continuous manner is thus carried out by addition of alkane and sulphur trioxide as and when they are consumed and the amount of alkanesulphonic acid withdrawn, while maintaining the molar ratio (alkane of formula $C_nH_{2n+2}$)/(sulphur trioxide) comprised between 4/1 and 2/1, preferably between 3.5/1 and 2.5/1, typically about 3, and the molar ratio (alkanesulphonic acid)/(sulphur trioxide) between 70/30 and 95/5, as previously indicated.

The reactor of the present invention can therefore favourably comprise several on-line analysers making it possible to continuously monitor the different contents of species present in the reaction system in order to block, if required, the intake and draw-off valves necessary for the proper conduct of the reaction according to the parameters defined above.

The process according to the present invention has many advantages, among which it is possible to cite, in addition to the fact that it is carried out continuously, good selectivity, and therefore the generation of a small amount of undesirable by-products, or even no undesirable by-products.

The process of the present invention is preferably carried out under substantially anhydrous conditions, and it is preferred to use a reaction solvent (alkanesulphonic acid) containing the smallest amount of water possible, or even an anhydrous alkanesulphonic acid. Likewise, sulphur trioxide is preferred in anhydrous form, the use of oleum, which is a mixture of sulphur trioxide and sulphuric acid, is not preferred in the process of the present invention.

Without intending to be bound by theory, the presence of water may generate sulphuric acid, a by-product which may be undesirable, in which case it is necessary to provide a separation step, for example by distillation, which results in additional production costs. The presence of traces of water, especially from the radical initiator, may however be acceptable provided the sulphuric acid, by-product in stoichiometric amount in relation to the water present, is withdrawn continuously with the alkanesulphonic acid formed. Once all the water has been consumed, the sulphuric acid by-product will no longer be formed.

The process of the present invention can therefore, quite easily be carried out continuously, by continuously adding alkane and sulphur trioxide and continuously withdrawing the alkanesulphonic acid formed.

Another advantage of the process of the present invention lies in the fact that the sulphur trioxide is present in the reaction medium in a very small amount, and in particular, in a much smaller amount than that found in patent application EP1558353. Indeed, and without intending to be bound by the theory, the reaction kinetics of alkane with sulphur trioxide is relatively slow, and it appears advantageous to carry out the reaction of alkane with sulphur trioxide in a diluted medium. This increases the selectivity and thus prevents the formation of undesirable by-products.

The alkanesulphonic acid withdrawn from the reactor outlet may contain more or less significant amounts of unreacted initial products (alkane and sulphur trioxide). These can be easily separated from the alkanesulphonic acid formed by stripping, for example by thermal stripping, and thus very advantageously to be easily re-injected into the reaction medium.

The alkanesulphonic acid thus produced according to the process of the present invention is characterized by high purity, greater than 95%, advantageously greater than 98%, and even greater than 99%.

In particular, the alkane-sulphonic acid formed is free of by-product and may be used, as is, without need for purification, by conventionally used techniques, mainly distillation and/or recrystallization. "Free" refers to impurity content below 1% by weight.

The process of the present invention is particularly suitable for the continuous industrial synthesis of methanesulphonic acid from methane and sulphur trioxide in a methanesulphonic solvent medium. Hence, and according to a particularly preferred embodiment, the solvent is methanesulphonic acid, the alkane is methane and the continuously withdrawn product is methanesulphonic acid.

Alkane-sulphonic acids are useful in many areas of application, for example, and to mention only a few applications of methanesulphonic acid, cleaning, catalysis, synthesis as reagent for the preparation of molecules or intermediates for the synthesis of molecules, and others.

More specifically, regarding methanesulphonic acid, it can therefore advantageously be used as is or subjected to a thermolysis step at a temperature of about 200° C. to 400° C., as indicated, for example, in the patent application EP1558353, to form methanol on the one hand and sulphur dioxide on the other hand, the sulphur dioxide being very favourably be regenerated sulphur trioxide which can be re-introduced into the synthesis reactor of the process of the present invention.

The invention also relates to the process for synthesizing methanol comprising the steps a) to f) described above wherein the solvent is methanesulphonic acid and the alkane is methane, and a step g) of heating to form sulphur dioxide on the one hand and methanol on the other.

Finally, the invention is aimed at a reaction medium comprising an alkane sulphonic acid of formula $C_nH_{2n+1}SO_3H$, where n is an integer between 1 and 20 inclusive, preferably between 1 and 12 inclusive, more preferably between 1 and 6 inclusive, and for example equal to 1, 2 or 3, sulphur trioxide $SO_3$, and an alkane of formula $C_nH_{2n+2}$, where n is a reaction medium as defined above, wherein: the molar ratio (alkanesulphonic acid)/($SO_3$) is comprised between 70/30 and 95/5, and the molar ratio (alkane)/($SO_3$) is comprised between 4/1 and 2/1, preferably between 3.5/1 and 2.5/1, typically equal to about 3.

Most preferably, the present invention relates to a reaction medium comprising methanesulphonic acid ($CH_3SO_3H$), sulphur trioxide $SO_3$, and methane ($CH_4$) wherein:

the molar ratio (methanesulphonic acid)/(sulphur trioxide) is comprised between 70/30 and 95/5, and the molar ratio (methane)/(sulphur trioxide) is comprised between 4/1 and 2/1, preferably between 3.5/1 and 2.5/1, typically equal to about 3.

The aforementioned reaction medium comprising an alkane sulphonic acid, sulphur trioxide $SO_3$, and an alkane may also comprise other species, among which it is possible to cite especially water, sulphuric acid, radical initiator and/or its decomposition products. These other species, when present, are most often in the form of traces, and more precisely their respective contents do not exceed 1% by weight in relation to the total weight of the reaction medium, preferably do not exceed 1000 ppm weight in relation to the total weight of the reaction medium.

EXAMPLE

The following process is implemented:
a) loading methanesulphonic acid (AMS) into an agitated continuous reactor under pressure in stabilized operation,
b) heating the methanesulphonic acid at a temperature of about 50° C.,
c) introducing a quantity of sulphur trioxide so that the molar ratio (AMS)/(sulphur trioxide) is 80/20,
d) introducing methane under pressure,
d) continuously introducing the initiator $CH_3$—$SO_2OO$—$SO_2OH$,
e) continuously conducting the reaction, simultaneously, sequentially or alternatively performing the following three sub-steps e1), e2) and e3):
e1) addition of sulphur trioxide in order to maintain the molar ratio (AMS)/(sulphur trioxide) of 80/20,
e2) addition of methane in order to maintain a molar ratio (methane)/(sulphur trioxide) of about 3, and
e3) continuous withdrawal of the methanesulphonic acid.

The invention claimed is:
1. A process for the continuous industrial preparation of alkanesulphonic acid of formula $C_nH_{2n+1}SO_3H$ from the alkane of formula $C_nH_{2n+2}$, wherein n represents an integer between 1 and 20 inclusive, said process comprising at least the following steps:
   a) loading of alkanesulphonic acid $C_nH_{2n+1}SO_3H$, wherein n is as defined above, in a reactor,
   b) heating said alkanesulphonic acid at a temperature between 25° C. and 120° C., c) introducing a quantity of sulphur trioxide so that the molar ratio (alkanesulphonic acid)/(sulphur trioxide) is between 70/30 and 95/5,
d) introducing the alkane under a pressure between 4 MPa and 15 MPa,
e) introducing a radical initiator,
f) continuous conducting of the reaction, and simultaneously or in any order performing the following three sub-steps f1), f2) and f3):
f1) addition of sulphur trioxide in order to maintain the initial molar ratio (alkanesulphonic acid)/(sulphur trioxide) defined in step c),
f2) addition of alkane in order to maintain a molar ratio (alkane)/(sulphur trioxide) between 4/1 and 2/1, and
f3) continuous withdrawal of the alkanesulphonic acid of formula $C_nH_{2n+1}SO_3H$, and
g) recovery of the alkanesulphonic acid of formula $C_nH_{2n+1}SO_3H$ after optional separation of unreacted reagents, and optionally any undesired by-products.

2. The process according to claim 1, wherein the reaction temperature is between 25° C. and 70° C.

3. The process according to claim 1 wherein the reaction pressure is between 5 MPa and 12 MPa.

4. The process according to claim 1, wherein the reactor is selected from reactors equipped with a recirculation loop, self-suction turbine reactors, reactors equipped with a venturi system, rotary bed reactors, and tubular reactors.

5. The process according to claim 1, wherein the radical initiator is selected from azo-bis-iso-butyronitrile, inorganic or organic peroxides, mercury sulphate, palladium sulphate, caesium sulphate, $K_2P_2O_8$, $CaO_2$, halogens, wherein n is as previously defined, the initiators of formula $C_nH_{2n+1}SO_2$—O—O—$SO_2OX$, wherein n is as defined above and X is hydrogen, an alkali or alkaline earth metal, zinc or aluminium, Caro acid and its salts with one or more alkali or alkaline earth metals, and Marshall acid and its salts with one or more alkali or alkaline earth metals.

6. The process according to claim 1, wherein alkane and sulphur trioxide are added as they are consumed and the amount of alkanesulphonic acid withdrawn, while maintaining the molar ratio (alkane of formula $C_nH_{2n+2}$)/(sulphur trioxide) between 3.5/1 and 2.5/1, and the molar ratio (alkanesulphonic acid)/(sulphur trioxide) between 70/30 and 95/5.

7. The process according to claim 1, wherein the solvent is methanesulphonic acid, the alkane is methane, and the continuously withdrawn product is methanesulphonic acid.

8. A reaction medium comprising an alkane sulphonic acid of formula $C_nH_{2n+1}SO_3H$, wherein n is an integer between 1 and 20 inclusive, sulphur trioxide $SO_3$, and an alkane of formula $C_nH_{2n+2}$, wherein n is as previously defined, said reaction medium, in which:
the molar ratio (alkanesulphonic acid)/($SO_3$) is between 70/30 and 95/5, and
the molar ratio (alkane)/($SO_3$) is between 4/1 and 2/1.

9. The reaction medium of claim 8, comprising methanesulphonic acid ($CH_3SO_3H$), sulphur trioxide $SO_3$, and methane ($CH_4$) wherein:
the molar ratio (alkanesulphonic acid)/($SO_3$) is between 70/30 and 95/5, and
the molar ratio (methane)/($SO_3$) is between 3.5/1 and 2.5/1.

* * * * *